(12) United States Patent
Finn et al.

(10) Patent No.: US 10,417,322 B2
(45) Date of Patent: Sep. 17, 2019

(54) REAL-TIME COLLABORATIVE CLINICAL DOCUMENT ANALYSIS AND EDITING

(71) Applicant: CERNER INNOVATION, INC., Kansas City, KS (US)

(72) Inventors: Christopher S. Finn, Liberty, MO (US); Steven S. Crooks, Gladstone, MO (US); David P. McCallie, Jr., Stilwell, KS (US); Margaret Cushing Kolm, Kansas City, MO (US); David J. O'Larte, Peculiar, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 360 days.

(21) Appl. No.: 15/148,589

(22) Filed: May 6, 2016

(65) Prior Publication Data

US 2017/0322919 A1 Nov. 9, 2017

(51) Int. Cl.
| | |
|---|---|
| *G06F 17/00* | (2019.01) |
| *G06F 17/24* | (2006.01) |
| *H04L 29/08* | (2006.01) |
| *G16H 15/00* | (2018.01) |

(52) U.S. Cl.
CPC ........... *G06F 17/241* (2013.01); *G16H 15/00* (2018.01); *H04L 67/10* (2013.01)

(58) Field of Classification Search
CPC ..................................................... G06F 17/241
See application file for complete search history.

(56) References Cited

U.S. PATENT DOCUMENTS

| | | | | |
|---|---|---|---|---|
| 6,575,901 | B2* | 6/2003 | Stoycos | A61B 5/044 600/300 |
| 7,613,620 | B2* | 11/2009 | Salwan | G06F 19/3418 705/2 |
| 9,251,235 | B1* | 2/2016 | Hurst | G06F 17/30581 |
| 9,552,407 | B1* | 1/2017 | Hurst | G06F 16/275 |
| 2004/0205448 | A1* | 10/2004 | Grefenstette | G06F 17/3061 715/230 |
| 2007/0192140 | A1* | 8/2007 | Gropper | G16H 10/60 705/3 |
| 2009/0132285 | A1* | 5/2009 | Jakobovits | G06F 3/0482 705/3 |
| 2010/0306249 | A1* | 12/2010 | Hill | G06Q 30/02 707/769 |
| 2011/0202370 | A1* | 8/2011 | Green, III | G06F 19/328 705/3 |

(Continued)

*Primary Examiner* — Laurie A Ries
(74) *Attorney, Agent, or Firm* — Shook, Hardy & Bacon L.L.P.

(57) ABSTRACT

Methods, computer systems, and computer storage media are provided for providing real-time analysis and annotation of clinical documents in a distributed system. A clinical transformation session is opened at a clinical transformation server maintaining sessions for one or more editors and agents operating on a clinical document. Sequences of operations on the clinical document are stored at a memory accessible by the server. At least a portion of the clinical document is analyzed in real-time to provide annotations and other document modifications to each of the one or more editors having a session at the server. Parallel annotations or modifications are resolved and a synchronized view of the clinical document is maintained based on operational transformation.

18 Claims, 4 Drawing Sheets

(56) References Cited

U.S. PATENT DOCUMENTS

| | | | |
|---|---|---|---|
| 2012/0215560 A1* | 8/2012 | Ofek | G06Q 10/10 |
| | | | 705/3 |
| 2013/0054512 A1* | 2/2013 | Ephrat | G06F 19/325 |
| | | | 707/602 |
| 2013/0173284 A1* | 7/2013 | Hyde | G06Q 50/22 |
| | | | 705/2 |
| 2013/0246130 A1* | 9/2013 | Michel | G06Q 10/067 |
| | | | 705/7.36 |
| 2014/0278448 A1* | 9/2014 | Sadeghi | G06Q 50/22 |
| | | | 705/2 |
| 2015/0134600 A1* | 5/2015 | Eisner | G06F 17/30011 |
| | | | 707/608 |
| 2017/0103558 A1* | 4/2017 | Sharma | G06T 11/60 |
| 2017/0300634 A1* | 10/2017 | Chiang | G06Q 50/24 |
| 2018/0075192 A1* | 3/2018 | Sethumadhavan | G06Q 10/10 |
| 2018/0286500 A1* | 10/2018 | Sole Guerra | G16H 10/60 |

* cited by examiner

REAL-TIME COLLABORATIVE CLINICAL DOCUMENT ANALYSIS AND EDITING

BACKGROUND

During the process of producing clinical documentation, an author may desire instantaneous feedback and analysis of the document they are composing. In cases where the clinical documentation tool can invoke logic to perform those checks within the same computing process (i.e., by calling local code to examine the current document state), the logic must be coded and updated in conjunction with the editing code, creating a linkage that makes it difficult to update or extend capabilities without requiring additional distribution of code. In a network environment, where the authoring tool is in a browser, local code execution involving complex logic is not always feasible, requiring analysis to be performed on a server that provides results back to the client.

In both cases, analysis is only performed on a document authored by a single user, and typically requires submission of the entire document from the client to the analysis process. If multiple analysis steps are required, systems typically call the steps in sequence.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to providing real-time analysis and annotation of clinical documents in a distributed system. A clinical transformation session is opened at a clinical transformation server maintaining sessions for one or more editors and agents operating on a clinical document. Sequences of operations on the clinical document are stored at a memory accessible by the server. At least a portion of the clinical document is analyzed in real-time to provide annotations and other document modifications to each of the one or more editors having a session at the server. Parallel annotations or modifications are resolved and a synchronized view of the clinical document is maintained based on operational transformation.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, an author producing clinical documentation may desire instantaneous feedback and analysis of the document being composed. In cases where the clinical documentation tool can invoke logic to perform those checks within the same computing process (i.e., by calling local code to examine the current document state), the logic must be coded and updated in conjunction with the editing code, creating a linkage that makes it difficult to update or extend capabilities without requiring additional distribution of code. In a network environment, where the authoring tool is in a browser, local code execution involving complex logic is not always feasible, requiring analysis to be performed on a server that provides results back to the client. In either case, analysis can only be performed on a document authored by a single user. Further, analysis typically requires submission of the entire document from the client to the analysis process.

Embodiments of the present invention enable real-time collaborative clinical document analysis and editing. To do so, one or more instances of an editing client process edit and/or operate (e.g., typing, dictation, and the like) on the same clinical document. An operational transformation server maintains sessions for all editors and agents operating on the document. An optional local memory cache stores sequences of operations upon the document. One or more analysis agents analyze the full document (or changes to the document) and provide annotations (in an inline or standoff fashion) and other document modifications back to all editors and agents with access to the document in real-time. Additionally or alternatively, other agents may monitor the work-in-progress documentation storage subsystem to provide transformation of documentation to other storage and representation formats in an electronic health record (EHR). For example, the documentation may be transformed to a proprietary, EHR-specific documentation format, or to an open, interoperable format.

Accordingly, in one aspect, an embodiment of the present invention is directed to one or more computer storage media having computer-executable instructions embodied thereon, that when executed, perform a method of real-time analysis and annotation of clinical documents in a distributed system. The method comprises opening a clinical transformation session at a clinical transformation server maintaining sessions for one or more editors and agents operating on a clinical document. The method also comprises storing sequences of operations on the clinical document at a memory accessible by the server. The method further comprises analyzing, by the agents maintained by the server, at least a portion of the clinical document in real-time to provide inline annotations and other document modifications to each of the one or more editors having a session at the server.

In another aspect of the invention, an embodiment is directed to one or more computer storage media having computer-executable instructions embodied thereon, that when executed, perform a method of real-time analysis and annotation of clinical documents in a distributed system. The method comprises establishing, by an agent, a clinical transformation session at a clinical transformation server. The clinical transformation session enables the agent to analyze the clinical document in real-time at least a portion of the clinical document. The method also comprises receiving, at the agent, the annotations or other document modifications from the one or more editors of the clinical document. The method further comprises providing, by the agent, annotations and other document modifications to each of the one or more editors having a session at the server. The method also comprises resolving parallel annotations or modifications to and maintaining a synchronized view of the clinical document for each of the editors based on operational transformation.

In a further aspect, an embodiment is directed to a system environment that enables real-time analysis and annotation of clinical documents in a distributed system. The system comprises one or more processors; and a non-transitory computer storage media storing computer-useable instructions that, when used by the one or more processors, cause the one or more processors to: open a clinical transformation session, at a clinical transformation server maintaining sessions for one or more editors and agents operating on a clinical document; store sequences of operations on the clinical document, at a memory accessible by the server; analyze at least a portion of the clinical document in real-time to provide annotations and other document modifications to each of the one or more editors having a session at the server; and resolve parallel annotations or modifications and maintain a synchronized view of the clinical document based on operational transformation.

Figure 1:
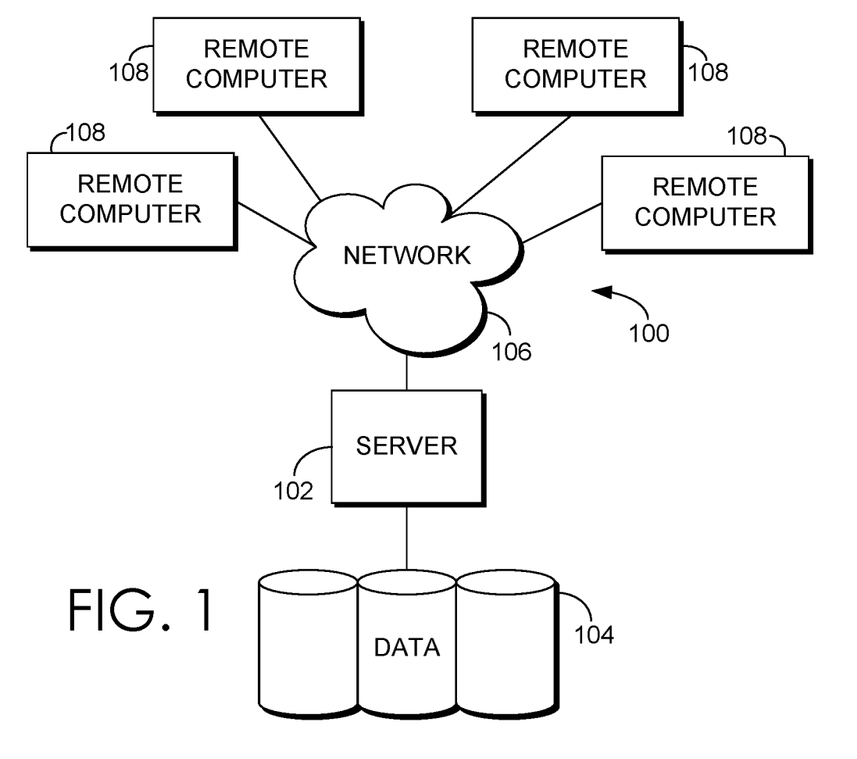
FIG. 1 is a block diagram of an exemplary computing environment suitable for use in implementing the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
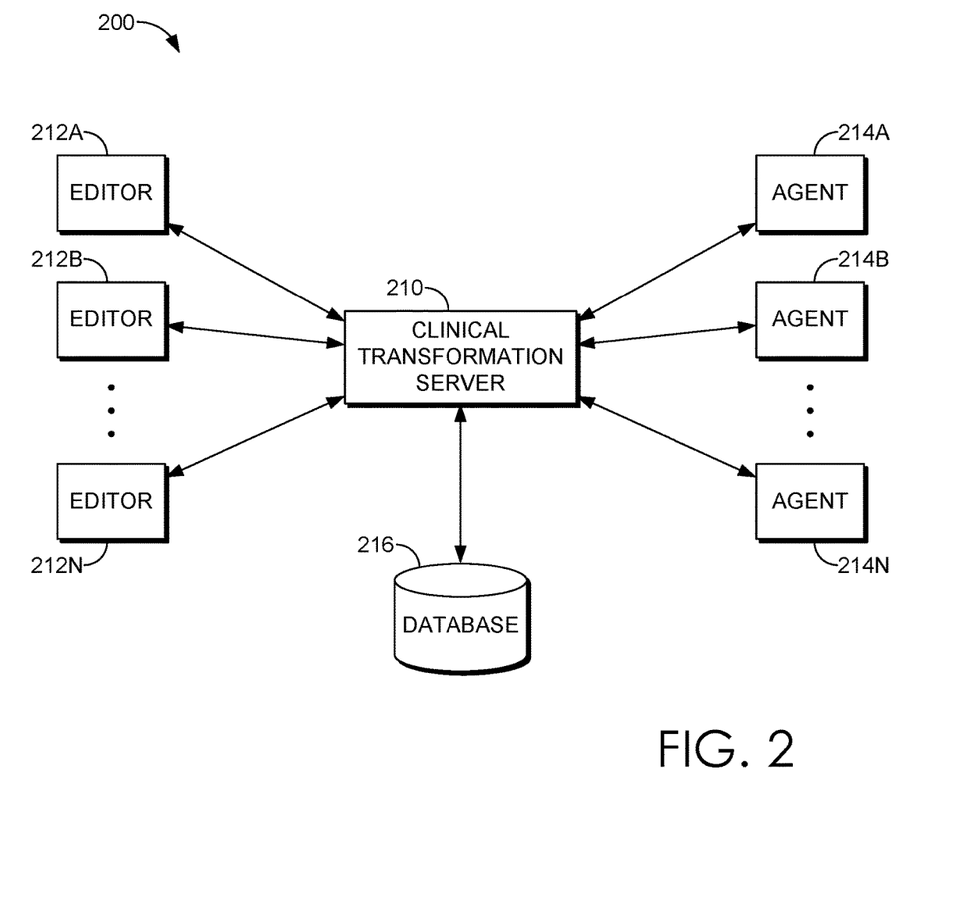
FIG. 2 is a block diagram of an exemplary system including a clinical transformation server, in accordance with an embodiment of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a clinical transformation server 210, editor(s) 212A-212N, agent(s) 214A-214N, and a database 216 (e.g., an EHR), all in communication with one another via a network (not shown in FIG. 2). The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

In some embodiments, one or more of the illustrated components/modules may be implemented as stand-alone applications. In other embodiments, one or more of the illustrated components/modules may be distributed across multiple clinical transformation servers. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the clinical transformation server 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The database 216 is configured to provide information to and store information communicated by, for example, the clinical transformation server 210 (e.g., sequences of operations on a clinical document). The information stored in association with the database 216 is configured to be searchable for one or more items of information stored in association therewith. The information stored in association with the database 210 may comprise information received from or used by various components of the clinical transformation server 210. Although illustrated in FIG. 2 as a single database 216, it is contemplated that multiple databases may be utilized by the present invention. In this way data and context may be aggregated from multiple sources (e.g., EHRs) or multiple locations.

The database 216 may store EHRs of patients associated with one or more healthcare facilities. EHRs may comprise electronic clinical documents such as images, clinical notes, orders, summaries, reports, analyses, information received from clinical transformation server 210 and medical devices (not shown in FIG. 2), or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The content and volume of such information in the database 216 is not intended to limit the scope of embodiments of the present invention in any way. Further, though illustrated as a single, independent component, the database 216 may, in fact, include a plurality of applications and/or storage devices, for instance, a database cluster.

The editor(s) 212A-212N may be any type of computing device capable of communicating via the network 202 with the clinical transformation server 210 to edit or annotate documentation stored in the database 216 and made accessible via the clinical transformation server 210, such as via a session. Such devices may include any type of mobile and portable devices including cellular telephones, personal digital assistants, tablet PCs, smart phones, and the like.

The agent(s) 214A-214N may be any automated process stored on any computing device (e.g., the editor(s) 212A-212N, the clinical transformation server 210, or a standalone computing device) to perform automated edits or annotations on documentation stored in the database 216 and made accessible via the clinical transformation server 210, such as via a session. In this regard, the agent(s) 214A-214N may be remote (processes running on other machines and accessed via a network protocol) or local (processes running locally and accessed by either a network protocol or inter-process communication mechanism). Additionally, the agent(s) 214A-214N may "scale out" and subscribe to specific types of documents.

Clinical transformation server 210 may include a processing unit, internal system memory, and a suitable system bus for coupling various system components, including one or more data stores for storing information (e.g., files and metadata associated therewith). The clinical transformation server 210 typically includes, or has access to, a variety of computer-readable media.

The computing system environment 200 is merely exemplary. While the clinical transformation server 210 is illustrated as a single unit, it will be appreciated that the clinical transformation server 210 is scalable. For example, the clinical transformation server 210 may in actuality include a plurality of computing devices in communication with one another. The single unit depictions are meant for clarity, not to limit the scope of embodiments in any form.

Initially, the clinical transformation server 210 opens a clinical transformation session for one or more edits or agents operating on a particular document. Sequences of operations on the clinical document are stored at a memory (e.g., database 216) accessible by the clinical transformation server 210. The operations are specifically tailored to clinical documents, and unlike normal document editing and/or annotation. For example, as illustrated below, clinical documents are highly specialized and require very particular information in particular fields. At least a portion of the clinical document may be analyzed in real-time to provide annotations and other document modifications to each of the one or more editors having a session at the server so the document is up-to-date for all editors, which is particularly important for clinical documents (where multiple clinicians may be interacting with various portions of the document at the same time).

One example of an operation performed by agents operating on clinical documents might include monitoring a document for possible errors in text or typing. Other operations might include monitoring a document for unsafe medical abbreviations. For example, a number of abbreviations are banned or discouraged by the Joint Commission on the Accreditation of Healthcare Organizations (JCAHO) or healthcare institutions, because they could be misunderstood which leads to medication error. An example of this might include "per os" which is ambiguous. The agent might prompt an in-line annotation asking the clinician "did you mean . . . 'PO (by mouth)' or 'By left eye (OS)'?" In another example, a clinician may enter "blood ethanol (ETOH) was 0.2." In this instance, the agent might prompt an in-line annotation asking the clinician "did you mean '0.2'?" which is the recommended format for numeric values.

Another example of an operation performed by agents operating on clinical documents might include monitoring a clinical document for spelling errors. In this way, after a clinician enters "arrhythmia", the agent might prompt an in-line annotation asking the clinician "did you mean 'arrhythmia'?"

Possible errors in content or meaning (based on textual and shallow or deep semantic interpretation) or incorrect word choice are other examples of operations that can be monitored by agents operating on clinical documents. For example, speech recognition and auto-corrected typing might lead to a particular class of error: an entered word that is a correctly spelled English word, but not the intended word, although similar in sound of spelling. This is especially hazardous in a medical context, because the vocabulary contains many complex and similar words with different meanings. For example, if a clinician enters "perineal tendinitis," the agent might prompt an in-line annotation asking the clinician "did you mean 'peroneal tendinitis?'" because tendinitis of the perineum is extremely unlikely, whereas tendinitis of the peroneal region is common. In a similar way, if a clinician enters "possible hypertension," the agent might prompt an in-line annotation asking the clinician "did you mean 'possible hypotension'?" because the clinical document contains other mentions of hypotension but no mention of hypertension.

Another example of an operation performed by agents operating on clinical documents might include monitoring for contradictory information. Clinical documentation often uses standard phrases, which a clinician must remember to modify for a particular situation. However, the clinician might overlook this modification, leading to incorrect or contradictory information. This problem is exacerbated in electronic documentation by the use of macros, templates, and copying. Agents may identify these common phrases and evaluate their accuracy by comparing to other content in the clinical document. For example, the clinical document might contain "no respiratory symptoms" under a Review of Systems section, but the History of Present Illness section might include "cough." Thus, "no respiratory symptoms" might be a contradictory statement and the agent might prompt an in-line annotation asking the clinician if they meant "no respiratory symptoms (except as noted in HPI)?"

Additionally, the agents operating on clinical documents might monitor for possible errors in clinical documents as compared to other data available in the EHR. For example, a patient name or demographic may be incorrect. This might indicate a typing error or accidental documentation on the wrong patient, a common source of medical error. If a clinician enters "patient is a spry 6 y.o. Asian female" the agent might prompt with an in-line annotation stating "did you mean '60 y.o. Asian female? The current patient, Mrs. Yang, is 60 years old.'" Or, the clinician might enter "Mr. Smith comes to the clinic today for diabetes management"

and the agent might prompt with an in-line annotation stating "did you mean 'Mrs. Brown? The current patient is Jane Brown'".

In some embodiments, the agents operating on clinical documents monitor for phrases repeated from a previous clinical document. If text is copied from a previous note, the clinician is responsible for updating that documentation for accuracy. The agent might compare the document to other documents to identify copied text that has not been updated appropriately. For example, if a clinician enters "antibiotics day 4", the agent might prompt with an in-line annotation asking "did you mean 'antibiotics day 5? This phrase also appears in: Inpatient Progress Note, September 16 (yesterday) by Dr. Smith'". Of, the clinician might enter "patient was admitted from the ED last night" and the agent might prompt with an in-line annotation stating "this phrase also appears in: Inpatient Progress note September 16 (yesterday) by Dr. Smith".

The clinical transformation server 210 resolves parallel annotations or modifications and maintains a synchronized view of the clinical document based on operational transformation (OT). For example, if multiple editors and/or agents are editing or annotating the same clinical document at the same time, the clinical transformation server 210 is able to resolve conflicts and keep each editor up-to-date with a synchronized view of the clinical document.

To do so, the clinical transformation server 210 employs OT to allow multiple editors and/or agents to modify the state of a document and maintain a consistent, synchronized view regardless of the order the changes are received. OT permits changes to documents to be submitted as a concise set of transformation operations to the document. These transformation operations can then be composed with other submitted operations to resolve conflicts. Operations may consist of sequences of smaller constituent changes such as insert, delete, retain, annotate, position, highlight, etc. The clinical transformation server 210 receives changes from all editors and/or agents, resolves conflicts, and responds to editors and/or agents with operations to apply to remain in sync with the current state of the document.

Editors and/or agents working on a document submit operations (state changes) along with a unique document identifier to the clinical transformation server 210. The clinical transformation server 210 initially checks to see if the operation is applied to an up-to-date view of the document. If not, the clinical transformation server 210 transforms the proposed changes against prior changes, updates the current document state (optionally in a server-side, memory-based cache such as Redis), and responds with the set of operations that the document editor must apply to its current representation of the document to synchronize to the current state.

As described above, various clinical analysis agents may establish sessions with the clinical transformation server 210 as well. As changes to the document are received, these agents perform analysis either of the entire document, or of just the changes, depending on the agent's analysis goals. This analysis may result in annotation operations (or direct modifications) being submitted to the document for synchronization. For instance, an annotation may be added directing the document viewer/editor to highlight particular medical phrases. In some embodiments, the agent automatically corrects spelling errors by directly modifying the document. In some embodiments, the agent automatically expands shorthand phrases to boilerplate text. In some embodiments, the agent acts upon the document without altering it, for example, to display the document's current state through another mechanism, or store snapshots of it in a transformed format (without altering the shared state.)

The operational transformation server 210 brokers changes to the document being edited, sequencing received transactions and responding to all clients subscribed (i.e., having sessions) to the document. Editors and/or agents use operational transformation to resolve parallel changes or annotations and maintain a synchronized view of the document. Operations may optionally be retained along with a timestamp for each operation, permitting later workflow analysis or "playback" of an editing session.

Figure 3:
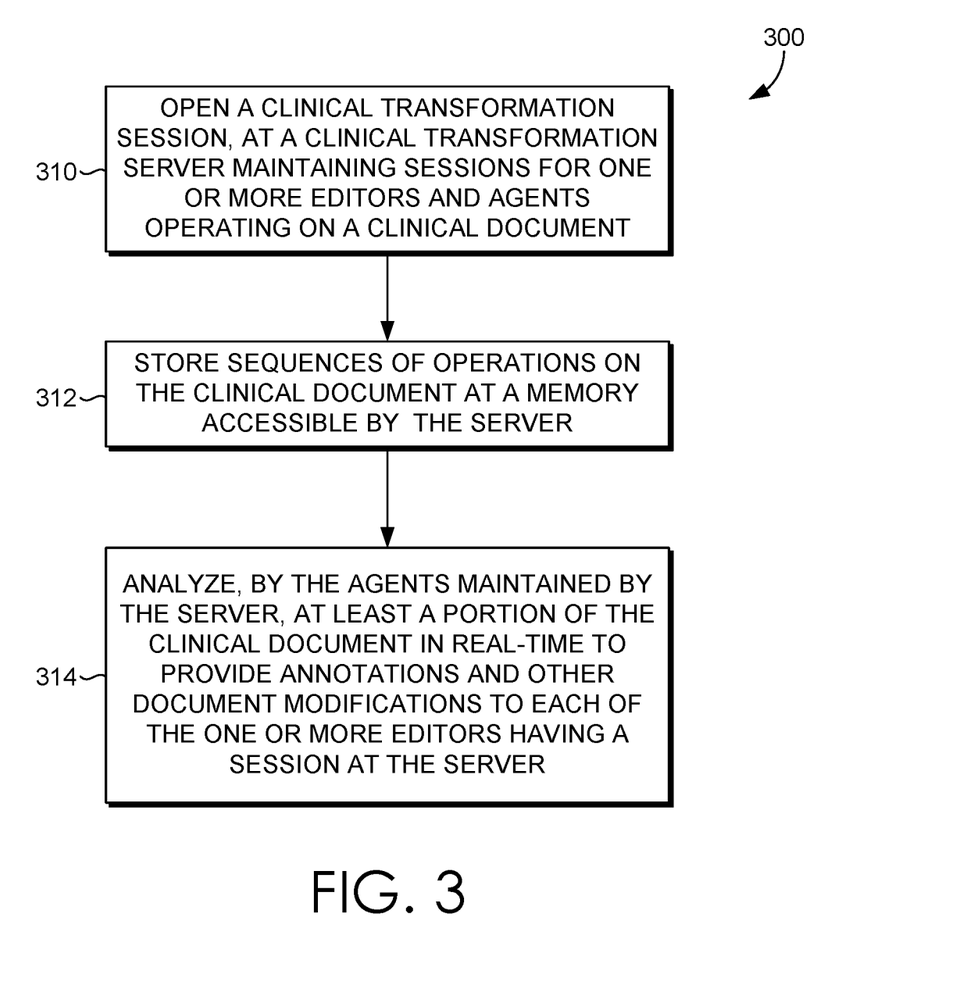
FIG. 3 is a flow diagram showing an exemplary method of real-time analysis and annotation of clinical documents in a distributed system, in accordance with various embodiments of the present invention.

Turning now to FIG. 3, a flow diagram is provided illustrating a method 300 of real-time analysis and annotation of clinical documents in a distributed system, in accordance with an embodiment of the present invention. Initially, as shown at step 310, a clinical transformation session is opened at a clinical transformation server. The clinical transformation server maintains sessions for one or more editors and agents operating on a clinical document. The editors may be users editing the document via a computing device, such as an editor 112A-112N shown in FIG. 2. In various embodiments, the agents monitor a document for: possible errors in text or typing, unsafe medical abbreviations, possible errors in content or meaning, incorrect word choice, contradictory information, or any combination thereof.

Sequences of operations on the clinical document are stored, at step 312, at a memory accessible by the server. In some embodiments, the clinical transformation server brokers changes to the clinical document being annotated or modified by sequencing received transactions and responding to each editor subscribed to the document. The one or more editors and agents may utilize operational transformation to resolve parallel annotations or modifications to the clinical document. Additionally or alternatively, the one or more editors and agents may utilize operational transformation to maintain a synchronized view of the clinical document.

At least a portion of the clinical document is analyzed, at step 314, by the agents maintained by the server. In some embodiments, the at least a portion of the clinical document comprises the clinical document in its entirety. In some embodiments, the at least a portion of the clinical document comprises only portions of the clinical document that have been annotated or modified. Annotations and other document modifications are provided to each of the one or more editors having a session at the server. In some embodiments, the annotations or other document modifications to the clinical document include a timestamp which may enable workflow analysis or playback of an editing session.

In some embodiments, the annotations or other document modifications from one or more editors of the clinical document are received at an agent operating on the clinical document. Decision support may be triggered based on the annotations or other document modifications to the clinical document. In some embodiments, a documentation storage subsystem is monitored at an agent operating on the clinical environment to provide transformation of documentation to other storage and representation formats in an electronic health record.

Figure 4:
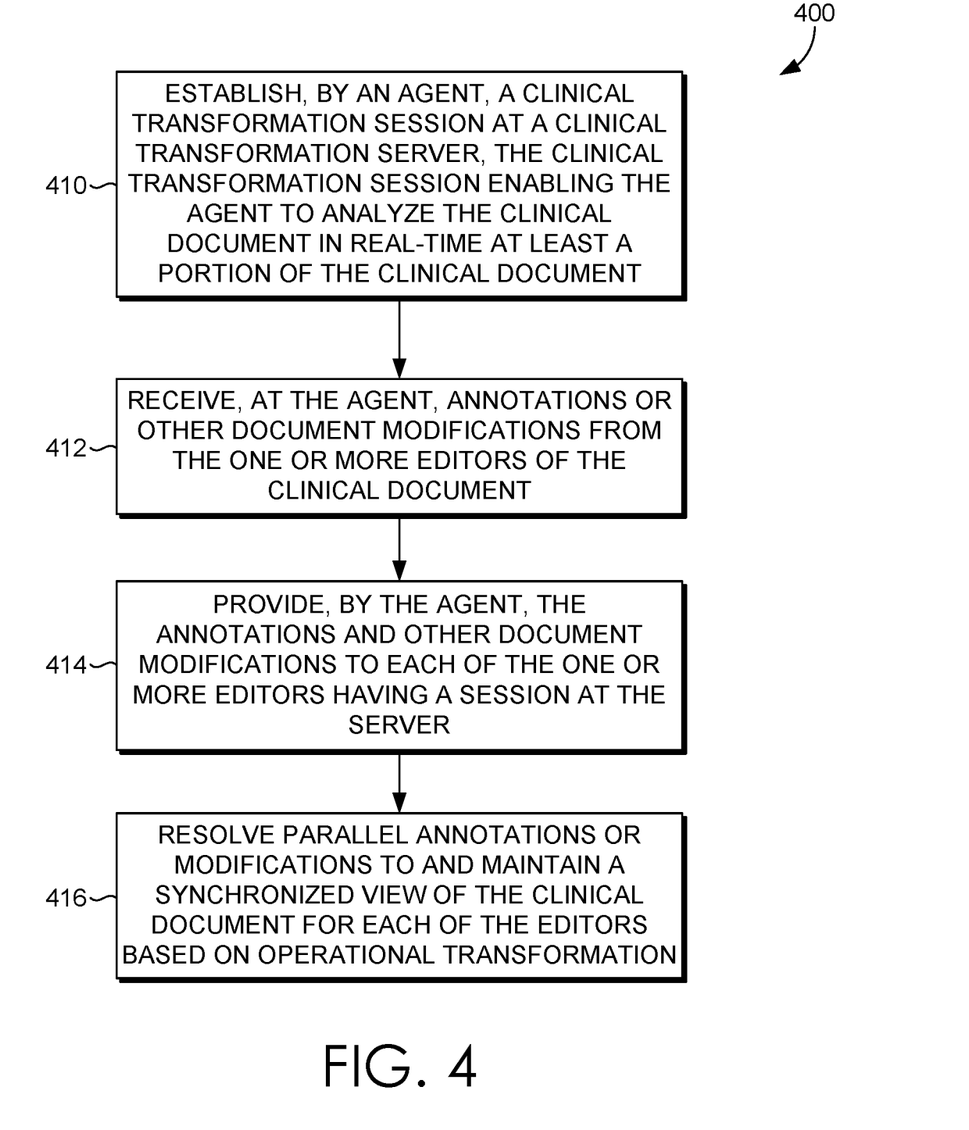
FIG. 4 is a flow diagram showing an exemplary method of real-time analysis and annotation of clinical documents in a distributed system, in accordance with various embodiments of the present invention.

Referring now to FIG. 4, a flow diagram is provided illustrating a method 400 of real-time analysis and annotation of clinical documents in a distributed system, in accordance with an embodiment of the present invention. Initially, as shown at step 410, a clinical transformation session is established by an agent at a clinical transformation server. The clinical transformation session enables the agent to analyze the clinical document in real-time at least a portion of the clinical document. In some embodiments, the agent monitors a document for possible errors in text or typing, unsafe medical abbreviations, possible errors in content or meaning, incorrect word choice, or contradictory information. In some embodiments, the agent monitors a documentation storage subsystem to provide transformation of documentation to other storage and representation formats in an electronic health record.

At step 412, the annotations or other document modifications from the one or more editors of the clinical document are received at the agent. Annotations and other document modifications are provided by the agent, at step 414, to each of the one or more editors having a session at the server. Parallel annotations or modifications to are resolved and a synchronized view of the clinical document is maintained, at step 416, for each of the editors based on operational transformation.

As can be understood, the present invention provides systems, methods, and user interfaces for providing real-time analysis and annotation of clinical documents in a distributed system. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media having computer-executable instructions embodied thereon, that when executed, perform a method of real-time analysis and annotation of clinical documents in a distributed system, the method comprising:
    opening a clinical transformation session at a clinical transformation server maintaining sessions for one or more editors and agents operating on a clinical document;
    storing sequences of operations on the clinical document at a memory accessible by the server;
    analyzing, by the agents maintained by the server, at least a portion of the clinical document in real-time to provide inline annotations and other document modifications to each of the one or more editors having a session at the server, wherein an agent of the agents monitors for errors in the clinical document as compared to data available in an electronic health record (EHR); and
    monitoring, at an agent operating on the clinical document, a documentation storage subsystem to provide transformation of documentation to other storage and representation formats in the EHR.

2. The media of claim 1, wherein the at least a portion of the clinical document comprises the clinical document in its entirety.

3. The media of claim 1, wherein the at least a portion of the clinical document comprises only portions of the clinical document that have been annotated or modified.

4. The media of claim 1, further comprising receiving, at an agent operating on the clinical document, the annotations or other document modifications from one or more editors of the clinical document.

5. The media of claim 4, further comprising triggering decision support based on the annotations or other document modifications to the clinical document.

6. The media of claim 1, wherein the annotations or other document modifications to the clinical document include a timestamp.

7. The media of claim 6, wherein the timestamp enables workflow analysis or playback of an editing session.

8. The media of claim 1, wherein the clinical transformation server brokers changes to the clinical document being annotated or modified by sequencing received transactions and responding to each editor subscribed to the document.

9. The media of claim 8, wherein the one or more editors and agents utilize operational transformation to resolve parallel annotations or modifications to the clinical document.

10. The media of claim 9, wherein the one or more editors and agents utilize operational transformation to maintain a synchronized view of the clinical document.

11. The media of claim 1, wherein the agents monitor a document for possible errors in text or typing.

12. The media of claim 1, wherein the agents monitor a document for unsafe medical abbreviations.

13. The media of claim 1, wherein the agents monitor a document for possible errors in content or meaning.

14. The media of claim 1, wherein the agents monitor a document for incorrect word choice or contradictory information.

15. One or more computer storage media having computer-executable instructions embodied thereon, that when executed, perform a method of real-time analysis and annotation of clinical documents in a distributed system, the method comprising:
    establishing, by an agent, a clinical transformation session at a clinical transformation server, the clinical transformation session enabling the agent to analyze in real-time at least a portion of a clinical document, wherein the agent monitors for errors in the clinical document as compared to data available in an electronic health record (EHR);
    receiving, at the agent, annotations or other document modifications from the one or more editors of the clinical document;
    providing, by the agent, the annotations and other document modifications to each of the one or more editors having a session at the server; and
    resolving parallel annotations or modifications to and maintaining a synchronized view of the clinical document for each of the editors based on operational transformation.

16. The media of claim 15, wherein the agent monitors a document for possible errors in text or typing, unsafe medical abbreviations, possible errors in content or meaning, incorrect word choice, similarity to other documents, contradictory information, inappropriate copy-and-paste of clinical notes, inappropriate duplication, or other forms of textual analysis.

17. The media of claim 15, wherein the agent monitors a documentation storage subsystem to provide transformation of documentation to other storage and representation formats in an electronic health record.

18. A computerized system comprising:
one or more processors; and
- a non-transitory computer storage media storing computer-useable instructions that, when used by the one or more processors, cause the one or more processors to:
- open a clinical transformation session, at a clinical transformation server maintaining sessions for one or more editors and agents operating on a clinical document;
- store sequences of operations on the clinical document, at a memory accessible by the server;
- analyze at least a portion of the clinical document in real-time to provide annotations and other document modifications to each of the one or more editors having a session at the server, wherein an agent of the agents monitors for errors in the clinical document as compared to data available in an electronic health record (EHR); and
- resolve parallel annotations or modifications and maintain a synchronized view of the clinical document based on operational transformation.

* * * * *